US011547461B2

(12) United States Patent
Keller et al.

(10) Patent No.: US 11,547,461 B2
(45) Date of Patent: Jan. 10, 2023

(54) METHOD AND DEVICE FOR CONTROLLING A TREATMENT PROCESS

(71) Applicant: Aesculap AG, Tuttlingen (DE)

(72) Inventors: Anton Keller, Dürbheim (DE); Stefan Eick, Tuttlingen (DE); Thomas Maser, Zimmern ob Rottweil (DE)

(73) Assignee: Aesculap AG, Tuttlingen (DE)

( * ) Notice: Subject to any disclaimer, the term of this patent is extended or adjusted under 35 U.S.C. 154(b) by 1318 days.

(21) Appl. No.: 15/522,019

(22) PCT Filed: Oct. 23, 2015

(86) PCT No.: PCT/EP2015/074596
§ 371 (c)(1),
(2) Date: Apr. 26, 2017

(87) PCT Pub. No.: WO2016/066542
PCT Pub. Date: May 6, 2016

(65) Prior Publication Data
US 2017/0333110 A1  Nov. 23, 2017

(30) Foreign Application Priority Data

Oct. 31, 2014 (DE) ...................... 10 2014 115 868.7

(51) Int. Cl.
*A61B 18/12* (2006.01)
*A61B 18/00* (2006.01)
(52) U.S. Cl.
CPC ............... *A61B 18/1206* (2013.01); *A61B 2018/00642* (2013.01); *A61B 2018/00672* (2013.01);
(Continued)

(58) Field of Classification Search
CPC ...... A61B 18/1206; A61B 2018/00642; A61B 2018/00672; A61B 2018/00702;
(Continued)

(56) References Cited

U.S. PATENT DOCUMENTS 6,733,498 B2  5/2004 Paton et al.
9,414,882 B2  8/2016 Tanaka et al.
(Continued)

FOREIGN PATENT DOCUMENTS

CN           1638700 A    7/2005
CN         102378601 A    3/2012
(Continued)

OTHER PUBLICATIONS

Notification of Reasons for Rejection for Japanese Application No. 2017-523198, dated Oct. 30, 2017, including English language translation, 22 pages.

(Continued)

*Primary Examiner* — Eun Hwa Kim
*Assistant Examiner* — Catherine Premraj
(74) *Attorney, Agent, or Firm* — Christopher A. Rothe; Culhane Meadows, PLLC

(57) ABSTRACT

A method and device for controlling a treatment procedure includes a treatment tool, an energy source, and a controller. The controller controls the energy source such that in a first treatment phase, power fed into the material to be treated is controlled with an increasing course. An impedance detector determines the impedance course and/or the present impedance of the material to be treated, and recognizes the achievement of an impedance minimum. A timer is started upon recognition of an impedance minimum, and upon recognition of a further impedance minimum within the specific time interval, the timer is reset. If no new impedance minimum is detected within the specific time interval and (Continued)

the time interval expires, the controller switches the power control to constant power or to a power course with an altered gradient. Upon fulfilling a specific criterion, there is a switchover from power control to voltage control.

26 Claims, 2 Drawing Sheets

(52) U.S. Cl.
CPC .............. *A61B 2018/00702* (2013.01); *A61B 2018/00755* (2013.01); *A61B 2018/00767* (2013.01); *A61B 2018/00875* (2013.01)

(58) Field of Classification Search
CPC ........... A61B 2018/00755; A61B 2018/00767; A61B 2018/00875
See application file for complete search history.

(56) References Cited

U.S. PATENT DOCUMENTS

| | | |
|---|---|---|
| 2003/0158551 A1 | 8/2003 | Paton et al. |
| 2007/0173811 A1* | 7/2007 | Couture ............. A61B 18/1445 606/45 |
| 2008/0114351 A1 | 5/2008 | Irisawa et al. |
| 2010/0179534 A1* | 7/2010 | Podhajsky ......... A61B 18/1206 606/34 |
| 2011/0028963 A1 | 2/2011 | Gilbert |
| 2011/0144635 A1 | 6/2011 | Harper et al. |
| 2011/0160725 A1* | 6/2011 | Kabaya .............. A61B 18/1206 606/42 |
| 2013/0338665 A1 | 12/2013 | Tanaka et al. |
| 2014/0350548 A1* | 11/2014 | Schall ................ A61B 18/1206 606/40 |
| 2017/0333111 A1 | 11/2017 | Kabaya et al. |

FOREIGN PATENT DOCUMENTS

| | | |
|---|---|---|
| CN | 103997979 A | 8/2014 |
| EP | 2025297 A2 | 2/2009 |
| JP | 2008114042 A | 5/2008 |

OTHER PUBLICATIONS

Chinese Office Action for Chinese Application No. 201580059215.3, dated Apr. 17, 2019 with translation, 15 pages.
German Search Report with English language translation for Application No. 10 2014 115 868.7, dated Jul. 16, 2015, 13 pages.
International Search Report and Written Opinion for International Application No. PCT/EP2015/074596, dated Nov. 1, 2016, 9 pages.

\* cited by examiner

Suspension of the power increase during the heating phase

Exemplary course of the TFT process

METHOD AND DEVICE FOR CONTROLLING A TREATMENT PROCESS

RELATED APPLICATIONS

This application is the United States national phase entry of International Application No. PCT/EP2015/074596, filed Oct. 23, 2015, which is related to and claims the benefit of priority of German Application No. DE 10 2014 115 868.7, filed Oct. 31, 2014. The contents of International Application No. PCT/EP2015/074596 and German Application No. DE 10 2014 115 868.7 are incorporated by reference herein in their entireties.

FIELD

The invention relates to a method and a device for controlling a treatment procedure before, during or after a surgical or non-surgical, or therapeutic or non-therapeutic treatment of a material, for instance a tissue of a non-human or non-animal kind, possibly also of human or animal origin.

BACKGROUND

From U.S. Pat. No. 6,733,498 B2 a method is known for treating biological tissue while applying a high frequency voltage to electrodes of a surgical HF instrument (HF=high frequency), in which the tissue impedance is monitored. During a first stage, a minimum tissue impedance value is detected and a relative tissue impedance is determined. Here, it is detected when the relative tissue impedance reaches a predetermined value, and then a switchover to a second stage occurs, with the duration of the second stage being calculated as a function of the duration of the first stage. Also during the second stage, a high frequency voltage is applied to the electrodes of the treatment tool.

From EP 2 025 297 A2, an electrical treatment system is known whose treatment tool is fed with high frequency energy during a first treatment phase for the conglutination of tissue. In a second treatment phase, a desiccation process for dehydrating the treated tissue is carried out. A controller switches over from the first treatment phase to the second treatment phase if a phase difference signal is detected. In this process, the application of the high frequency energy is terminated if the phase difference detected during the second treatment phase exceeds a predetermined phase difference value.

Nevertheless, problems may arise in case of a premature or a delayed transition from the first treatment phase to the second treatment phase.

SUMMARY

The invention is based on the object to provide a device and a method with which a material treatment such as a tissue treatment can be carried out effectively.

The features and configurations, which are described or illustrated below, of exemplary embodiments of the device according to the invention or the method according to the invention also apply, vice versa, to possible design configurations of the method according to the invention or the device according to the invention, even if this is not explicitly indicated.

In one aspect, the invention relates to a device intended for controlling a treatment procedure and comprising a treatment tool, in particular an electrical fusion apparatus such as a surgical HF instrument, and an impedance detection means. By means of an energy source, electric power is introduced into material to be treated by the treatment tool. Control means for controlling the energy source is configured to control the energy source in such a manner that in a first treatment phase the power fed into the material to be treated is controlled in a closed-loop manner, preferably with a ramp-shaped, e.g. linear, exponential, sigmoidal or logarithmic course. The closed-loop control of the power instead of the voltage ensures that the power input into the tissue will not be too high, and on the other hand an effective, controllable impact on the tissue can occur and the impedance can be reduced in a stable manner.

The control means of the device is configured to control the energy source such that during or after the first treatment phase upon fulfillment of a preferably integral criterion a switchover occurs from power control to voltage control or impedance control. In one or more of the described exemplary embodiments, an impedance control is performed via the voltage control.

The impedance detection means is capable of determining the impedance course and/or the present impedance of the material to be treated and reliably detecting the achievement of an impedance minimum. Here, one or more of the described exemplary embodiments may involve the use of digital or analog filters (e.g. low-pass filters) for filtering out rapid transients from the impedance signal.

As an option, a timer is started in regular or irregular intervals and/or upon recognition of an impedance minimum, wherein the timer is set to a specific time interval. Upon recognition of an impedance reduction or a first or further impedance minimum within the specific time interval, the timer may be reset again and begin to run again. If no new impedance minimum is recognized within the specific time interval and the time interval expires, the timer generates a signal causing the control means to switch preferably from power control to constant power or optionally to a power course with an altered, e.g. extremely reduced gradient or dropping power. This criterion does not have to be necessarily reached during an HF treatment, but serves to guard against an excessively high power input, if the tissue temperature is near the evaporation temperature.

Upon fulfillment of the preferably integral criterion which will be described in more detail below, a switchover occurs from power control to voltage control, so that it is the electric voltage now which is the controlled variable. This allows to prevent undesirably large or too small voltages which could have an adverse effect on the treatment. In this context, it is not necessary that an intervention in the form of a power limitation has occurred beforehand.

In one or more of the described exemplary embodiments, the device and the method are configured to limit the temporal voltage increase and/or power increase.

The impedance detection means may be configured to determine the impedance course and/or the present impedance of the material to be treated and to recognize the achievement of an impedance minimum, wherein in one or more of the described exemplary embodiments a timer which may be set to a specific time interval may be started in regular or irregular intervals and/or upon recognition of an impedance minimum. Upon recognition of an impedance reduction or a first or further impedance minimum within the specific time interval, the time may be reset again and start to run again, wherein the timer optionally generates a signal causing the control means to switch over the power control to constant power or to a power course with an altered gradient, whenever no new impedance minimum is recognized within the specific time interval and the time interval expires.

In one or more of the described exemplary embodiments, the device may be configured to change over from voltage control to power control again, if the impedance again drops for a predefined time and/or a new impedance minimum is detected.

In one or more of the described exemplary embodiments, the integral criterion is a temporal integral over the impedance increase with respect to the smallest measured impedance. Here, a switchover from power control to voltage control may occur if the temporal integral reaches a threshold value, so that the integral criterion is able to react to very fast and also to slow impedance changes or impedance alterations.

As an option, the device or method—upon switching over from power control to voltage control—is configured to detect the voltage just applied and to reduce the voltage set value to be used for the voltage control by a specific value or percentage of e.g. 2 to 70%, preferably 5 to 20%, so that the voltage set value to be used for the voltage control will amount to e.g. 50% to 98%, or 80% to 95% of the voltage prevailing at the point of switching.

As an option, the device or method may also be configured to measure the initial tissue impedance in an initial phase preferably with very small power, so that an impedance change due to a temperature change does not occur yet.

As an option, the device or method may also be configured to use an integral criterion for the switchover to keeping the power constant, for which the temporal integral over the impedance increase is determined with respect to the smallest impedance that has been measured hitherto, and the switchover occurs as soon as the temporal integral ($Zs(n)$) reaches a threshold value. Here, a quotient may be formed from the temporal integral and the smallest impedance in order to obtain a standardization on a respective impedance level.

As an option, the device or method may also be configured to carry out an impedance acceleration after a transition into a keeping phase, in which the gradient of the impedance (Z) is increased, for instance in linear fashion, with the option that the HF voltage U may serve as a control variable for controlling the impedance.

According to a further aspect of the invention, the method for controlling a treatment procedure with the aid of a treatment tool, in particular a surgical HF instrument, involves to control an energy source in such a manner that in a first treatment phase a closed-loop control of the power fed into the material to be treated takes place with an increasing, e.g. ramp-shaped, preferably linear course, then, optionally upon response of a criterion which recognizes that the impedance has not dropped any more or has only slightly dropped for a predetermined time, a switchover occurs to a power control with constant power or to a power course with an altered gradient, and then after a further time interval a switchover occurs from the power control to voltage control.

In this process, the present impedance of the material to be treated and/or the impedance course can be determined and the achievement of an impedance minimum can be recognized: A timer set to a specific time interval may be started in regular or irregular intervals and/or upon recognition of an impedance minimum. The timer—upon recognition of an impedance reduction or of a first or a further impedance minimum within the specific time interval—may be reset again and begin to run again. Optionally, if no new impedance minimum is detected within the specific time interval and the time interval expires, the timer may generate a signal which causes to switch over the power control to constant power or to a power course having an altered gradient. In a variant of the design, the power or the power increase is preset as a function of the initial impedance and the present impedance. It is preferred that the ratio between the present impedance and the initial impedance is used for this purpose.

In one or more of the described exemplary embodiments, a limitation of the temporal voltage increase may be made during the power control. This achieves a power limitation or power reduction, if the tissue impedance rises fast or suddenly. This prevents or eliminates the occurrence of tissue bursts.

The device may be also be arranged to change over from the voltage control to the power control, if the impedance again drops for a predefined time and/or a new impedance minimum is detected.

During the switchover from power control to voltage control, the voltage just applied may be reduced by a specific value or percentage of e.g. 2 to 70%, or 5% to 20%.

In one or more of the described exemplary embodiments, the voltage is changed in the switchover from power control to voltage control such that the power changes by a percentage of e.g. 1 to 70%.

In one or more of the described exemplary embodiments, the initial tissue impedance is optionally measured in an initial phase, preferably with very small power, wherein the initial tissue impedance is measured in the initial phase for instance with a power which amounts to e.g. only 0.1 to 3 Watt or 0.1 to 10% of the power initially used in the subsequent power control.

In one or more of the described exemplary embodiments, the power increase may be a function of the present value of the temporal integral.

Furthermore, the power increase may be selected in one or more of the described exemplary embodiments in the first treatment phase as a function (i.e. depending on) the initial impedance and/or the present impedance.

In one or more of the described exemplary embodiments, the power increase in the first treatment phase may be selected for instance depending on the ratio between the present impedance and the initial impedance. The power or the power increase may be preset in one or more of the described exemplary embodiments for instance as a function of the initial impedance and the present impedance; here, the ratio between the present impedance and the initial impedance is preferably used.

During the first treatment phase, i.e. during power control, a limitation of the temporal voltage increase may occur in one or more of the described exemplary embodiments.

In one or more of the described exemplary embodiments, there may again be a changeover from voltage control to power control if the impedance drops again for a predefined period of time and/or a new impedance minimum is detected.

According to a further aspect of the invention, a device implemented in software or hardware is provided, which comprises means for carrying out the method according to one, more or all of the measures set out above or below.

BRIEF DESCRIPTION OF THE DRAWING FIGURES

The invention will be described in more detail below on the basis of exemplary embodiments with reference to the drawings.

DETAILED DESCRIPTION

An integral criterion for recognizing an impedance minimum is described first, which is used or can be used with an exemplary embodiment of the method according to the invention and/or of the device according to the invention.

To this end, the behavior of biological tissue during a treatment with high-frequency alternating current of e.g. 300 kHz to 1 MHz is described first, which is a customary practice in an HF treatment (HF stands for high frequency). The tissue to be treated may also be a non-biological type. In this context, the temperatures, the impedance behavior and tissue modifications are looked at in order to illustrate peculiarities of a thermal treatment method by means of high frequency or of a fusion process.

Figure 2:
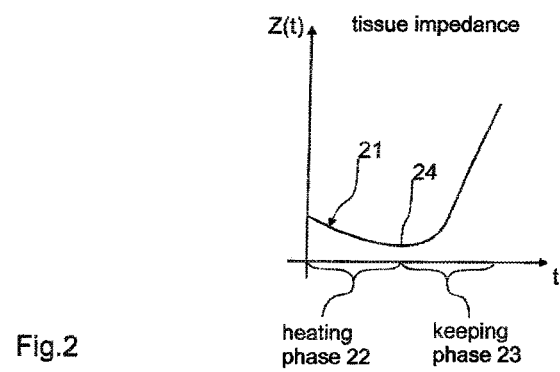
FIG. 2 shows a course of the tissue impedance during a treatment.

In general, the heating of biological or also non-biological tissue, for instance with the aid of electric current, results in a characteristic behavior of the impedance as is exemplarily shown in FIG. 2. The ordinate of the diagram according to FIG. 2 shows the impedance Z, whereas the abscissa shows the time t. The impedance curve is provided with the reference symbol 21. In FIG. 2, the heating phase is marked with the reference symbol 22, whereas the keeping phase is provided with the reference numeral 23.

First, the impedance drops as a rule, which may be attributed to the fact that a biological tissue is an ion conductor having a negative temperature coefficient. In such case, the impedance is reduced till that point where the tissue liquids begin to evaporate.

This is usually the lowermost point 24 of the impedance curve 21 which is shown in FIG. 2 and also referred to as a bathtub curve, which is reached for instance at a tissue temperature of approximately 90° C. In case of further heating the tissue, the impedance Z continually increases as a rule. This results from the fact that the water vapor generated through the evaporation has a poor conductivity and the conductive water is expelled out of the tissue, so that there is a desiccation phase. These two phases may be referred to as a heating phase 22 and keeping phase 23, for example. Accordingly, the heating of the tissue up to the point of evaporation of the water occurs in the heating phase 22, whereupon in the following keeping phase 23 the temperature is maintained or only slightly increased.

The moment 24 of the transition from the heating phase 22 to the keeping phase 23 is a critical point during controlling and regulating an HF treatment process. At this moment 24, the boiling temperature of the tissue water is reached, so that it transitions very fast from the liquid phase into the vapor phase. It was realized that abruptly escaping vapor may result in bursting tissue, if the HF power (high frequency power) is not reduced in due time at that moment. During bursting, there is an exponential increase of the impedance as an electric characteristic. An excessively rapid transition from the heating phase 22 into the keeping phase 23 may additionally entail the danger of increased thermal damages ("thermal spread"), since rapidly escaping water vapor may thermally damage surrounding tissue.

As can be seen from FIG. 2, the impedance Z first drops in the heating phase 22 (phase 1), reaches its minimum and in many cases abruptly increases again in the keeping phase 23 (phase 2). Due to the fact that different ways of controlling and regulating may be used in the heating phase 22 (phase 1) and in the keeping phase 23 (phase 2), it is intended in the exemplary embodiments described here to precisely recognize the transition point 24 from phase 1 to phase 2, in order to be able to change between the two control programs or techniques or to carry out a corresponding switchover of the control method. Basically, it has turned out that the recognition of the transition point 24 is problematic, as there may be very different modes of behavior determined by the type of the tissue, the amount of the tissue, the humidity of the electrodes and so on. An erroneous recognition results in undesired effects in the process progress, wherein a distinction can be made between a premature and a delayed switchover of the process.

With a premature switchover, a switchover to the second control phase (phase 2) occurs for instance in the event of a supposed recognition of an impedance minimum, in which a closed-loop control of the impedance course can be carried out. In the event of a premature switchover, the closed-loop control expects an increase in the impedance with an increase of the power input, for instance by increasing the current and/or the voltage and/or the treatment intervals. However, as the impedance continues to drop with an incorrect assessment of the impedance minimum despite a higher power input, the deviation between the actually desired target trajectory of the impedance course and the really existing actual trajectory of the impedance course becomes increasingly larger. This results in an excessive power input which may bring about tissue damages.

On the other hand, a delayed switchover means that the switchover to the next control phase (phase 2) does not occur yet although the impedance minimum has already been passed and the impedance increases again (in some cases even in abrupt fashion), because not all conditions for the switchover are fulfilled, for example. Such a situation involves the danger that the tissue bursts because of the undiminished power, as the water is abruptly evaporated and/or expelled. As a consequence, there may be tissue damages in the form of burst tissue as well as heavy thermal spread and denaturized tissue, which cannot be sealed any more because of the missing liquid or humidity.

Thus, the disadvantages of such a premature or delayed switchover between the control phases may be tissue damages in the form of burst tissue, carbonized tissue, denaturized/desiccated tissue, a tissue adherence on electrodes and a heavy thermal spread.

An undesired, incorrect switchover between the control phases may be brought about by various problems or errors. By way of example, a burst in the tissue may result in a rapid increase in the impedance, after which the impedance decays again as in phase 1. This skip in the impedance, however, forms the basis of the danger of an incorrect premature recognition and an assessment as a minimum upon switching over the control.

Furthermore, there may occur the situation that the tissue passes several minima, which may happen for instance with those types of tissue that consist of two or more layers which are structurally different. By way of example, tissues of the esophagus or parts of the colon frequently exhibit two or more impedance intermediate minima in phase 1. In such a case, the impedance generally runs through the first minimum, then rises again for several seconds and again drops below the first minimum. The ratios of the minima and their temporal intervals may vary widely depending on the tissue. Also in such a case, there is the danger of a premature switchover into phase 2, although phase 1 is de facto not completed yet.

A further incident may occur in the form of a sudden impedance change, in which the impedance course in the sense of the impedance curve 21 according to FIG. 2 increases abruptly in many cases, in particular when treating a small amount of tissue. This is reflected by a sudden impedance change. In terms of control technology, however, such an occurrence could be identified as a tissue burst in the sense mentioned above and the switchover might be delayed through this.

Figure 1:
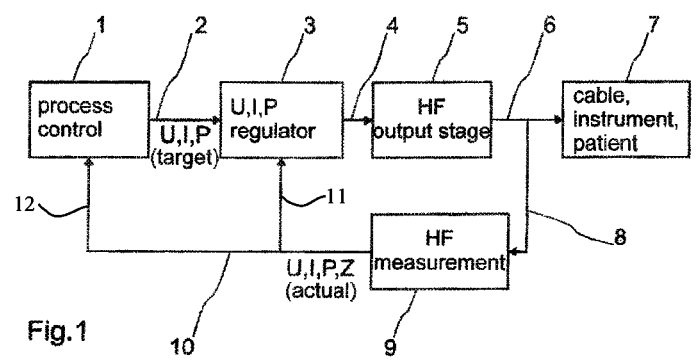
FIG. 1 shows an exemplary embodiment of a device according to the invention.

FIG. 1 shows an exemplary embodiment of a device according to the invention in the form of a block diagram which illustrates a process control and process regulation that avoid such errors. Thus, FIG. 1 shows a block diagram of the process control/closed-loop control.

The exemplary embodiment according to FIG. 1 comprises a process controller 1, a regulator 3, a high-frequency output stage 5 and a schematically indicated instrument 7 as well as a measuring device 9. The process controller 1 delivers input variables to the regulator 3 via a signal connection 2, for instance in the form of a line or a wireless communication. In one or more of the described exemplary embodiments, the process controller 1 and the U,I,P regulator 3 may be accommodated in a microprocessor. The input variables may be, for instance, one or more target values for the voltage U, the current I and/or the power P. The regulator 3 may act for example as a voltage regulator and/or current regulator and/or power regulator and supplies its output signal(s) via a signal connection 4, for instance in the form of a line or a wireless communication, to the high-frequency output stage 5 which outputs the drive signals for the instrument 7 via a signal connection 6 e.g. in the form of a wire or a wireless communication route. The signals which are output by the HF output stage 5 and are to be applied to the instrument 7 and/or the signals received by the instrument 7 are applied via a signal connection 8, for instance in the form of a line or a wireless communication link, to the measuring device 9 (HF measurement), which measures the signals applied to the instrument 7 and/or delivered by it and, at its output side, outputs the currently measured actual values of the voltage U and/or of the current I and/or of the power P and/or of the impedance Z via the signal connection 10, for instance in the form of a line or a wireless communication route, to a signal connection 11 connected to an input of the regulator 3 and implemented e.g. in the form of a line or a wireless communication, and applies them via the latter to an input of the regulator 3 as well as an input 12 of the process controller 1. This means that both the process controller 1 and the regulator 3 receive information on the prevailing values of the actual values of the current applied to the instrument 7 or measured there and/or of the voltage and/or power and/or impedance.

In the illustrated exemplary embodiment, the prevailing voltages, currents, the power and the tissue impedance are detected by the HF measuring device 9 which is located between the HF output stage 5 and the instrument 7 or the patient, and are passed on to the process controller 1. The process controller 1 acts as a power controller or as an impedance regulator in different process phases (phase 1, i.e. 22, and phase 2, i.e. 23). The process controller 1 delivers the default values for voltage, current and power of the U,I,P regulator 3 which regulates the HF output stage 5 such that none of the default values for the voltage, the current and/or the power is exceeded. This means that the process controller 1 and the regulator 3 can act as a cascaded control loop in which the process controller 1 forms the regulator of the external control loop, whereas the U,I,P regulator 3 forms the regulator of the internal control loop.

Figure 4:
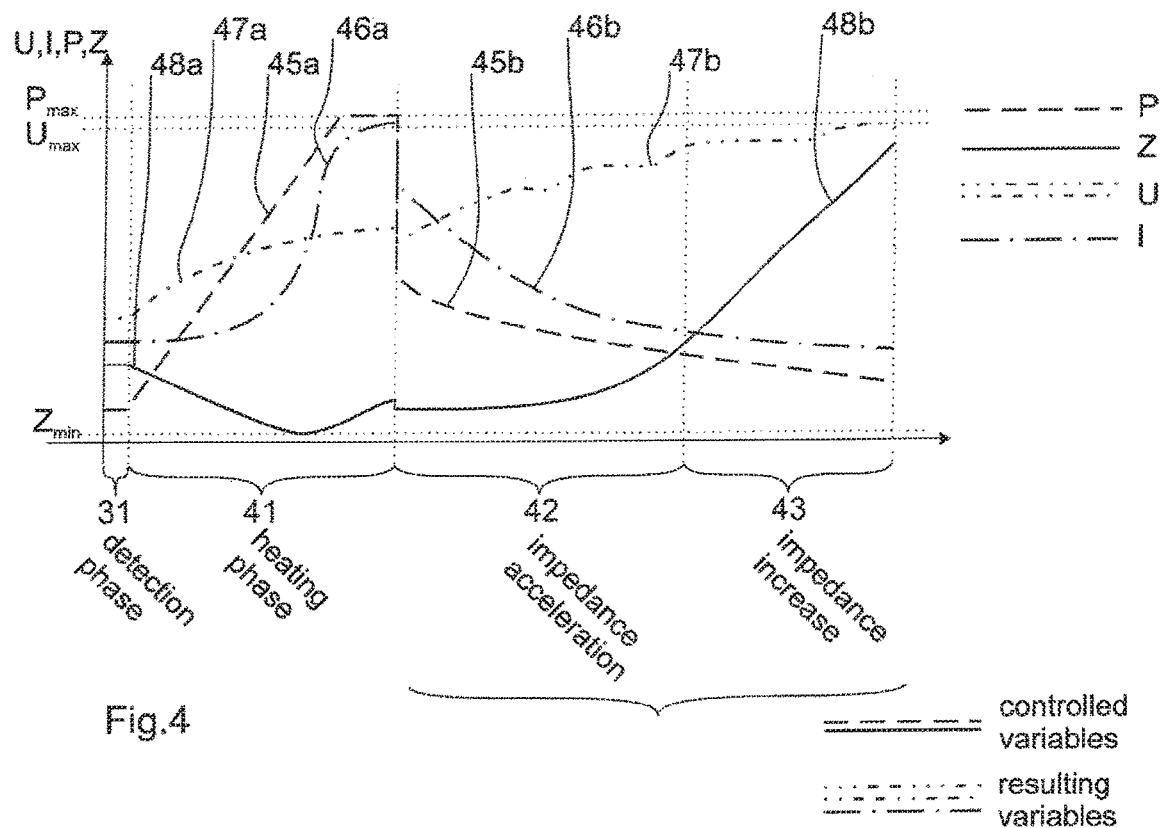
FIG. 4 shows a schematic progression of a treatment procedure using an exemplary embodiment of the device according to the invention and/or of the method according to the invention.

In the following, the operating principle of exemplary embodiments of the device according to the invention and/or of the method according to the invention will be exemplarily described on the basis of FIG. 4. FIG. 4 shows a typical course of a sealing process for the power P, see curve 45a, 45b; for the current I, see curve 46a, 46b; for the voltage U, see curve 47a, 47b; and for the tissue impedance Z, see curve 48a, 48b. These variables are linked with each other, so that they cannot be varied independently of one another. This is why the variables used for the closed-loop control are drawn in FIG. 4 with lines 45a, 48b, whereas the variables resulting therefrom are depicted with lines 45b, 46a, 46b, 47a, 47b, 48a. In the heating phase 41, the power P is regulated (curve 45a) and the impedance Z is observed (curve 48a), whereas in the keeping phase 42, 43 the impedance Z (curve 48b) is regulated while using the voltage U (curve 47b) as a control variable.

An embodiment of a method according to the invention which can be carried out with the exemplary embodiment of the device according to the invention illustrated in FIG. 1 will be explained in more detail below.

In an optional first step, a short-term detection is carried out which may also be referred to as a detection phase or sensing phase. The initial tissue impedance is measured during this first phase. The measurement can be carried out within a very short term of for instance only a few milliseconds such as 1 to 500 milliseconds. The power P during this first step is chosen here to be so small that no thermal tissue effect is brought about. The power may amount to approximately 0.1 to 5 Watt, for example. In general, the power $P(n)=P_m$ in this phase (n∈N) is chosen so as to have a correspondingly small value. The impedance value measured in this phase can be used for the further course of the process. This phase is carried out for a predefined measuring duration of e.g. 1 to 500 ms, i.e. for the predefined measuring duration. With this, said first phase, i.e. the first step is completed.

In a second step, a heating phase 22 as the second phase is carried out, wherein the method may also directly start with this second phase, i.e. with the heating phase, without carrying out the first phase.

Starting from the measured power $P_m$ applied with the first step or applied at the beginning of the heating phase, the high frequency power (which in the following is designated in abbreviated form as HF power and applied to the instrument) is increased until an impedance minimum is achieved. This procedure of increasing may occur in linear fashion, but in other cases also in a non-linear manner. This results in the following formulaic relation:

$$P(n)=P_m+\alpha_{PR}T_s*n.$$

In the afore-mentioned equation, the factor $\alpha_{PR}$ represents the power increase, whereas $T_s$ represents the sampling time. In this phase, particular attention is paid to the already mentioned, critical point 24 of the phase transition, as there is an increased danger of tissue damages in this process phase, i.e. the heating phase. In this phase, i.e. in the second step, an increasing HF power is used, as the tissue amount that has been gripped with the instrument 7 is not known at the starting time. In contrast to a constant power, this increasing HF power prevents the heating phase from lasting for a very long time, if the power adjustment is too small. This would entail the danger of tissue adherences. Simultaneously, the increasing HF power also prevents the heating phase from being completed too fast, for instance in split seconds, and prevents the tissue from bursting, in case the high frequency power (with constant power) has been chosen such that it is too high.

This approach provided in the exemplary embodiment allows to seek and find the correct power adjustment so to speak in an automatic fashion.

In order to prevent the already described sudden impedance change, provision is made in one or more exemplary embodiments of the invention that the procedure of increasing the high frequency power is not continued any more if the yet decreasing tissue impedance rises again or has not taken a new minimum value for a predefined time of e.g. $t_{P\ rise}$. For detecting the temporal duration since the impedance minimum detected most recently, a variable $t_{lastZmin}$ is provided. Accordingly, the following equation arises as a formula for controlling the HF power:

$$P(n) = P(n-1) + \frac{a}{T_s} \begin{cases} a = 0, & t_{last\ Zmin} > t_{P\ rise} \\ a = a_{PR}, & sonst \end{cases}$$

Thus, the HF power is kept constant and does not increase further if no new smaller minimum impedance has been measured for a defined time interval $t_{P\ rise}$, which means that the impedance has remained the same or has even increased again. In this case, it can be assumed that the process is near the "critical phase transition".

Figure 3:
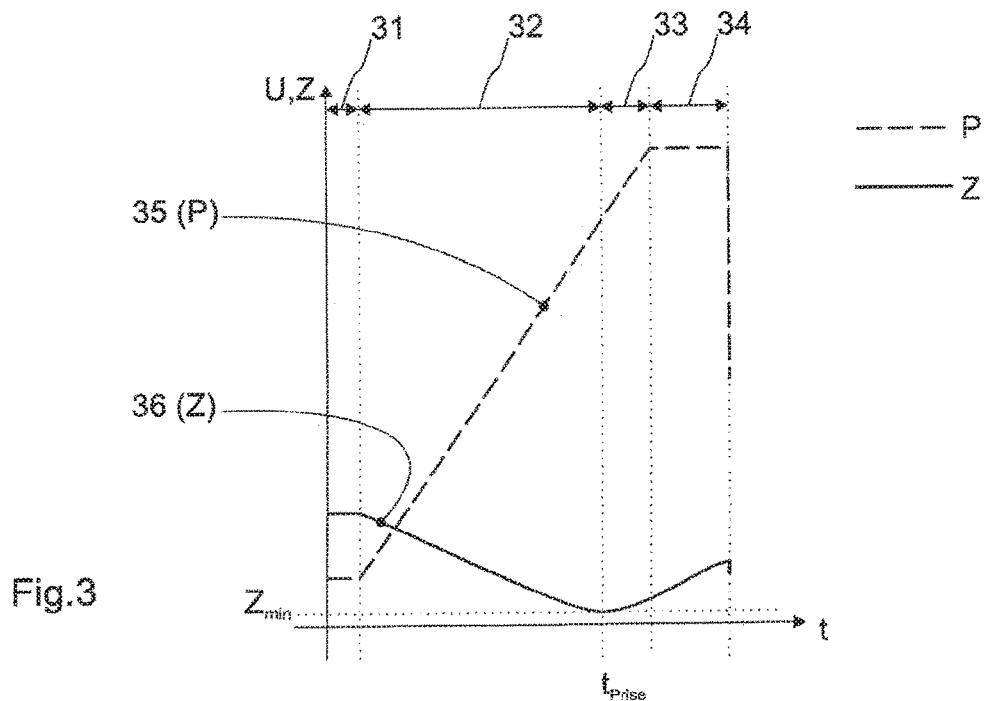
FIG. 3 shows details of an embodiment of a method according to the invention.

FIG. 3 shows an exemplary example for the power control during the heating phase (phase 2, or 22 in FIG. 2). As can be taken from FIG. 3 with the curved line 35 indicating the power, the power increase which increases at first essentially in linear fashion is switched over to a constant value which in the illustrated exemplary embodiment corresponds to the power value achieved so far; in deviation to this, said value may also be lower or higher.

The moment of switching over to keeping constant the power P which is fed into the instrument 7, see curved line 35, occurs after the point in time of the last detection of a minimum by the predefined time interval $t_{Prise}$ illustrated by the reference symbol 33, after which the impedance Z illustrated by the curved line 36 does not decrease further, but on the contrary even increases again in the illustrated exemplary embodiment.

In the exemplary embodiment according to FIG. 3, the power increase provided during the heating phase is suspended then and the achieved power is kept constant.

In FIG. 3, the reference symbols 31 to 34 designate the first, second, third and fourth phase of the power controller, respectively. The curve 35 indicates the controlled course of the power, whereas the curve 36 represents the impedance course Z. The ordinate shows the power P and the impedance Z, whereas the abscissa shows the time. In the optional phase 31, the initial impedance Z is measured while keeping the power constant for a short term, whereupon after expiration of the predefined period of time, or in another exemplary embodiment immediately at the start of the treatment, a linear power increase is provided in phase 2 designated with the reference symbol 32. The transition into the third phase designated with the reference symbol 33 and exhibiting a further increasing power P is characterized by the detection of the impedance minimum $Z_{min}$; thereupon, the third phase 33 is used for awaiting and checking if indeed no new, still deeper minimum is reached. After expiration of the phase 33, the switchover to keeping the power P constant occurs in the fourth phase 34.

An integral criterion capable of reacting to very fast and also slow impedance changes or impedance alterations serves for terminating the phase 32, 33.

The value $$Zs(n) = \sum_{n_{min}}^{n} (Z(n) - Z_{min}) \cdot T_s \begin{cases} Z_{min} = Z(n) \\ n_{min} = n \end{cases}, Z(n) < Z_{min}$$

is the temporal integral over the impedance increase with respect to the smallest impedance $Z_{min}$ that has been measured in a process at the time of n*Ts. The heating phase is finished as soon as Zs(n) reaches a threshold value. Zs(n) will be 0 if a new minimum impedance is reached in a process. This means that Zs(n) cannot reach the predefined threshold value in this case.

In above equation, it is not yet taken into consideration that a sealing process may take place at different impedance levels depending on the type of the tissue, its condition, its size and also depending on the instrument etc. For considering these circumstances, above equation may be rewritten into $$Zs(n) = \frac{\sum_{n_{min}}^{n}(Z(n) - Z_{min}) \cdot T_s}{Z_{min}} \begin{cases} Z_{min} = Z(n) \\ n_{min} = n \end{cases}, Z(n) < Z_{min}$$

Now, Zs(n) is obtained from the quotient of said integral and $Z_{min}$. This achieves a standardization on the respective impedance level where the process proceeds.

When the process has changed over from the heating phase (second phase) or phase 41 in FIG. 4 to the keeping phase 42, 43, the HF power will first be lowered in phase 42 by a specific factor (cf. FIG. 4) of e.g. 30% to 70%. This serves to compensate for the proceeding impedance change. The rapid lowering of the power also entails in most cases a small reduction of the impedance Z.

In this phase 42, 43 of the process, a closed-loop control aiming at an impedance trajectory is carried out, which is subdivided according to FIG. 4 in two sections:
  an impedance acceleration in phase 42
  an impedance increase (optionally with a constant gradient) in phase 43.

In the phase 42 of the "impedance acceleration", the gradient of the impedance Z is linearly increased. This measure serves for minimizing the thermal spread which might occur if too much water is evaporated too fast here. The duration of the impedance acceleration is predefined in terms of time. The phase 42 is completed if a predefined impedance has been reached.

The HF voltage U as a control variable serves for regulating the impedance. For calculating the HF output voltage $$U_{HF}(n) = U_{HF}(n-1) + \frac{\Delta U_{HF}}{T_s} \begin{cases} \Delta U_{HF} = \Delta U_{HF\ pos}, & Z(n) < Z_{soll}(n) \\ \Delta U_{HF} = \Delta U_{HF\ neg}, & Z(n) > Z_{soll}(n) \end{cases}$$

a distinction is made whether the present impedance Z(n) is above or below the target impedance Zsoll. Depending on this, the output voltage UHF is altered by a specific value $$\frac{\Delta U_{HF\,pos}}{T_s} \text{ or } \frac{\Delta U_{HF\,neg}}{T_s}.$$

The exemplary embodiment thus uses a power ramp in which the power is increased in a ramp-shaped fashion, i.e. increased with a constant gradient, wherein the power ramp is intermitted if no new minimum has been detected for a long time, whereupon a switchover occurs to constant power.

Thus, the power is linearly increased in the starting phase until the tissue is heated up, with the heating procedure being regarded as completed if the tissue impedance increases again after its minimum.

The steepness of the power curve is selected such that neither tissue bursts nor thermal damages nor a sudden desiccation of the tissue will appear.

In the exemplary embodiment, provision is made to increase the high frequency power P only as long as the tissue impedance is in the downward trend.

To this end, a timer is used which detects the period of time since the last impedance minimum. The timer is again reset to zero upon detecting an impedance minimum in each case and then starts to count anew. The timer is adjusted to a specific time interval and—in case of its expiry without an interim reset, i.e. without an interim detection of a new impedance minimum—outputs an output signal at whose occurrence the control means terminates the ramp-shaped power increase.

The linear power increase can be terminated upon achieving and/or exceeding a limit value. The limit value may be a temporal limit value, i.e. it may correspond to the time interval predefined by the timer, but it may also be a power-related limit value at the achievement of which the power increase is terminated or, if need be, continued to be carried out only with a considerably reduced gradient, i.e. in flatter fashion.

In a further exemplary embodiment, provision can be made to detect the period of time between the occurrences of minima of the impedance during the still linearly increasing power. If it is detected that the period of time between the occurrences of impedance minima becomes larger, but does not yet achieve the period of time predefined by the timer, the device according to the invention and the method according to the invention may also reduce the gradient of the power curve in one or more exemplary embodiments. This achieves a more gentle approach to the switching point at which a final switchover to constant power occurs when the timer has actually expired, i.e. if no new impedance minimum has been detected during the predetermined time interval.

As can be seen in FIG. 4, the closed-loop control of the power P is terminated (first in a ramp-shaped manner, then in a constant fashion) at the end of the heating phase, whereupon the power P does no longer represent the controlled variable in the following phases 42 with impedance acceleration and 43 with impedance increase. Instead, a switchover to voltage control occurs at this moment, in which the voltage is the control variable and is specifically increased by the microprocessor with the course increasing in a step-shaped manner. However, immediately upon switching over from power control with the power P as a control variable to the following regulation of the voltage with the voltage U as a control variable, the voltage U is specifically lowered, as can be seen in the area of the transition between the curve branches 47a, 47b (voltage U).

In phase 41, only the power P is the control variable, as illustrated by the curved line 45a, whereas the impedance Z, voltage U and current I ensue as a consequence of the local conditions and the targeted power control, see curves 46a (I), 47a (U) and 48a (Z).

During the phases 42, 43, only the voltage according to curve 47b is specifically regulated, whereas the curves 45b (power P), 46b (current I) and 48b (impedance Z) ensue as a consequence hereof.

The invention claimed is:

1. A device for controlling a treatment procedure comprising:
   a treatment tool;
   an impedance detector;
   an energy source for inputting electric power into a material to be treated by the treatment tool;
   a timer; and
   a controller for controlling the energy source, wherein the controller is configured to control the energy source in such a manner that in a heating phase, a control of power fed into the material to be treated takes place with an increasing ramp-shaped course until a tissue impedance measured by the impedance detector rises or has not taken a new minimum value for a predefined time, at which time the controller switches to control the energy source with constant power or to a power course with a different gradient, and the controller is configured to control the energy source in such a manner that in a keeping phase, a gradient of the tissue impedance measured by the impedance detector is increased in a linear fashion,
   wherein a changeover occurs from power control with constant power in the heating phase to voltage control or impedance control of the energy source in the keeping phase upon fulfilling an integral criterion, wherein in the keeping phase the voltage is a control variable and is increased with an increasing course in a step-shaped manner, and
   wherein the integral criterion is a temporal integral over an impedance increase with respect to a smallest measured impedance in the heating phase, and the changeover occurs from power control with constant power in the heating phase to voltage control or impedance control of the energy source in the keeping phase when the temporal integral over the impedance increase reaches a threshold value, so that the integral criterion is able to react to impedance changes or impedance alterations.

2. A device for controlling a treatment process, the device comprising:
   a treatment tool;
   an impedance detector;
   an energy source for inputting electric power into a material to be treated by the treatment tool;
   a timer; and
   a controller for controlling the energy source,
   wherein the controller is configured to control the energy source such that, during a heating phase, power fed into the material to be treated is regulated so as to have an increasing ramp-shaped course,
   wherein a changeover occurs from power control in the heating phase to voltage control or impedance control of the energy source in a keeping phase upon fulfilling an integral criterion, wherein in the keeping phase the voltage is a control variable and is increased with an increasing course in a step-shaped manner, and wherein the impedance detector is configured to determine at least one of an impedance course and a present impedance of the material to be treated, and to recognize achievement of an impedance minimum, the timer being started in the heating phase in regular or irregular intervals and/or being started upon recognition of the impedance minimum and set to a specific time interval, the timer, upon recognition of an impedance reduction or a first or further impedance minimum within the specific time interval is reset again and begins to run again, and the timer, when no new impedance minimum is detected within the specific time interval and the specific time interval expires, generates a signal which causes the controller to switch over from power control to a constant power or to a power course having an altered gradient.

3. A device for controlling a treatment process, the device comprising:
   a treatment tool;
   an impedance detector;
   an energy source for inputting electric power into a material to be treated by the treatment tool;
   a timer; and
   a controller for controlling the energy source,
   wherein the controller is configured to control the energy source such that, during a heating phase, power fed into the material to be treated is regulated so as to have an increasing ramp-shaped course until a tissue impedance measured by the impedance detector rises or has not taken a new minimum value for a predefined time, at which time the controller switches to control the energy source with constant power or to a power course with a different gradient,
   wherein a changeover occurs from power control with constant power in the heating phase to voltage control or impedance control of the energy source in a keeping phase upon fulfilling an integral criterion, wherein in the keeping phase the voltage is a control variable and is increased with an increasing course in a step-shaped manner, and
   wherein the device is configured to change over from voltage control to power control again when the tissue impedance measured by the impedance detector drops again for a predefined time and/or a new impedance minimum is recognized.

4. The device according to claim 1, wherein the device is configured to limit a temporal voltage increase.

5. The device according to claim 1, wherein the device is configured to reduce a voltage just applied by a specific value or percentage upon the changeover from power control in the heating phase to voltage control or impedance control in the keeping phase.

6. The device according to claim 1, wherein the device is configured to measure an initial tissue impedance in an initial phase with a very small power whereby no thermal tissue effect is brought about.

7. The device according to claim 1, wherein the temporal integral over the impedance increase is determined with respect to the smallest measured impedance and the changeover is made as soon as the temporal integral over the impedance increase reaches the threshold value.

8. The device according to claim 7, wherein the device is configured to form a quotient from the temporal integral over the impedance increase and the smallest measured impedance in order to obtain a standardization on a respective impedance level.

9. The device according to claim 7, wherein the device is configured to form a quotient from the temporal integral over the impedance increase and an initial impedance in order to obtain a standardization on a respective impedance level.

10. The device according to claim 1, comprising at least one of a digital filter or an analog filter, wherein a present tissue impedance is determined by a filtering by the at least one of a digital filter or an analog filter.

11. The device according to claim 1, wherein the device is configured to carry out an impedance acceleration after a transition to the keeping phase, in which a gradient of impedance is increased.

12. A method of controlling a treatment procedure using a treatment tool, the method comprising the steps of:
   controlling an energy source in such a manner that in a heating phase, a control of power fed into a material to be treated takes place with an increasing ramp-shaped course until a tissue impedance rises or has not taken a new minimum value for a predefined time and switching to power control with constant power or to a power course with a different gradient when the tissue impedance rises or has not taken a new minimum value for the predefined time; and
   switching from power control with constant power in the heating phase to voltage control of the energy source in a keeping phase upon fulfillment of an integral criterion, wherein in the keeping phase the voltage is a control variable and is increased with an increasing course in a step-shaped manner and a gradient of the tissue impedance increases in a linear fashion,
   wherein the integral criterion is a temporal integral over an impedance increase with respect to a smallest measured impedance in the heating phase, and a switchover occurs from power control to voltage control in the keeping phase when the temporal integral over the impedance increase reaches a threshold value, so that the integral criterion is able to react to impedance changes or impedance alterations.

13. The method according to claim 12, wherein:
   at least one of a present impedance of the material to be treated or an impedance course are determined, and an achievement of an impedance minimum is recognized,
   a timer set to a specific time interval is started in the heating phase in regular or irregular intervals and/or being started upon recognition of the impedance minimum,
   the timer, upon recognition of an impedance reduction or of a first or further impedance minimum within the specific time interval, is reset again and begins to run again,
   the timer, when no new impedance minimum is detected within the specific time interval and the specific time interval expires, generates a signal which causes a switchover from power control to a constant power or to the power course with the different gradient, and
   a switchover occurs from power control to voltage control or impedance control upon fulfillment of the integral criterion irrespectively of whether there has been a switchover from power control to constant power or to the power course with the different gradient.

14. The method according to claim 12, wherein when switching over from power control to voltage control, a voltage just applied is reduced by a specific value or percentage.

15. The method according to claim 12, wherein when switching over from power control to voltage control, voltage is changed such that power changes by a percentage.

16. The method according to claim 12, wherein in an initial phase, an initial tissue impedance is measured, and wherein the initial tissue impedance is measured in the initial phase with power which amounts to a percentage of power initially used in a following power control whereby no thermal tissue effect is brought about in the initial phase.

17. The method according to claim 12, wherein an integral criterion is used for switching to power control with constant power, for which purpose the temporal integral over the impedance increase is determined with respect to a smallest impedance which has been measured hitherto, and said switching to power control with constant power is carried out as soon as the temporal integral over the impedance increase reaches the threshold value.

18. The method according to claim 17, wherein a quotient of the temporal integral over the impedance increase and at least one of the smallest impedance and an initial tissue impedance is formed in order to obtain a standardization on a respective impedance level.

19. The method according to claim 17, wherein a power increase is a function of the temporal integral over the impedance increase.

20. The method according to claim 12, wherein a power increase in the heating phase is selected as a function of at least one of an initial impedance and a present impedance.

21. The method according to claim 20, wherein the power increase in the heating phase is selected depending on a ratio between the present impedance and the initial impedance.

22. The method according to claim 12, wherein a power or a power increase is predefined as a function of an initial impedance and a present impedance, for which a ratio between the present impedance and the initial impedance is used.

23. The method according to claim 12, wherein a limitation of a temporal voltage increase is effected during power control.

24. The method according to claim 12, wherein a changeover from voltage control to power control occurs when the tissue impedance drops again for a predefined period of time and/or a new impedance minimum is recognized.

25. The method according to claim 12, wherein an impedance acceleration is carried out during or after a transition to the keeping phase, in which the gradient of the impedance is increased.

26. A device for carrying out the method according to claim 12.

* * * * *